United States Patent [19]
Lambden

[11] Patent Number: 6,159,169
[45] Date of Patent: Dec. 12, 2000

[54] METHOD AND APPARATUS FOR MOVING NECK MUSCLES

[76] Inventor: Brian D. Lambden, P.O. Box 729, Englewood, Colo. 80151

[21] Appl. No.: 08/940,593

[22] Filed: Sep. 30, 1997

[51] Int. Cl.[7] ............................. A47C 20/02; A47C 20/08
[52] U.S. Cl. .................................. 601/15; 5/637; 5/640; D6/601; 601/25; 601/39; 601/134
[58] Field of Search .................................. 601/15, 25, 39, 601/57, 70, 134–8; 606/204; D6/601; 5/636, 637, 640

[56] References Cited

U.S. PATENT DOCUMENTS

| | | |
|---|---|---|
| D. 273,915 | 5/1984 | Pike . |
| D. 406,718 | 3/1999 | Jacobs . |
| 2,902,993 | 9/1959 | Wagner . |
| 3,981,032 | 9/1976 | Brooks . |
| 4,114,612 | 9/1978 | Benjamin . |
| 4,617,691 | 10/1986 | Monti et al. . |
| 4,770,466 | 9/1988 | Pesterfield . |
| 4,771,493 | 9/1988 | Park . |
| 5,163,195 | 11/1992 | Hill . |
| 5,481,771 | 1/1996 | Burk, IV . |

FOREIGN PATENT DOCUMENTS

| | | | |
|---|---|---|---|
| 2003319 | 11/1993 | Russian Federation | 601/134 |
| 18840 | 8/1912 | United Kingdom | 601/135 |

*Primary Examiner*—Danton D. DeMille
*Attorney, Agent, or Firm*—Sheridan Ross P.C.

[57] ABSTRACT

A method and apparatus is provided for treating whiplash injury. The apparatus comprises a base unit having an upright surface, a top surface and a bottom surface, wherein the upright surface adjoins the top surface and the bottom surface. The top surface declines radially to the bottom surface to allow rotation of a person's neck substantially coaxially along its own axis.

20 Claims, 2 Drawing Sheets

METHOD AND APPARATUS FOR MOVING NECK MUSCLES

FIELD OF THE INVENTION

The present invention is directed to an apparatus and a method for moving neck muscles to stretch and strengthen them for the purpose of treating whiplash associated disorders (WAD) and other neck conditions.

BACKGROUND OF THE INVENTION

Neck injuries, such as whiplash injury, are prevalent in our society. Although the exact number of whiplash injuries varies from one country to another, it is estimated that the incidence of whiplash injury is approximately 1 in 1000 people in western society. Bogduk et al., Pain, 1994, 58, 283. Whiplash injury is clinically defined as hyperextensionhyperflexion injury of the neck.

In almost all cases, whiplash injury is a result of motor vehicle accidents (MVA). It has been shown that the head is subject to marked rotational acceleration in the first 25 msec after the impact, followed by a reversal of the direction of acceleration as extension occurs. It is estimated that in a rear-end collision of an automobile at a moderate impact speed of 20 miles per hour (mph), the human head reaches a peak negative acceleration of 12 g, i.e., 12 times the gravitational force, and at an impact speed of 40 mph, the human head is subject to negative acceleration of 46 g during extension. Without being bound by any particular theory, it is believed that the neck dissipates force through shear and then torque which exceeds the tolerance levels of bone, muscle and ligament, leading to neck injury. The muscles that normally control the direction and amplitude of motion do not have time to respond to the forces applied to them in an MVA.

The primary symptoms of whiplash injury is either dull or a sharp pain over the back of the neck with associated neck stiffness or restricted movement. This pain is exacerbated by movement. In addition, some suffer headaches, visual disturbances, dizziness, weakness, paresthesia (tingling and numbness sensations), and/or cognitive difficulties as well as other physical and psychological problems.

The majority of whiplash injury patients recover within the first 2–3 months. However, it is estimated that between 14 and 42% of patients with whiplash injuries suffer chronic neck pain and 10% will have pain indefinitely. The economic impact related to WAD is significant due to medical costs and loss of productivity in many patients.

Currently, a variety of methods are used to treat whiplash injuries. One of the treatment methods is cervical epidural steroid injections, which can be hazardous, and some studies have shown that it is ineffective. Another method is drug therapy using analgesics, antiinflammatories or antidepressants. Medication can reduce the pain and/or inflammation but do not address any specific cause of pain. In addition, there is always the dangers of potential harmful side effects from the medication.

One study has shown that compared to rest and wearing a cervical collar, physiotherapy provided significant improvements in cervical movement and pain after 8 weeks. Mealy et al., Br. Med. J., 1986, 292, 656. Other studies have shown that a home exercise program was just as effective as out-patient physiotherapy. McKinney et al., Arch. Emerg. Med., 1989, 6, 27.

Physiotherapy of WAD involves several different techniques, one of which is stretching neck muscles and monitoring the progress of the patient's motion. Such physiotherapy is conducted by a therapist manually manipulating the head and neck of a patient. Typically, no apparatus is used for this treatment. Current methods of monitoring the progress of patients are time-consuming and subject to significant variability from one therapist to another. In addition, the expense and current limitations in health care plans to pay for physical therapy restricts the access of patients to therapists.

Therefore, there is a need for an apparatus for moving neck muscles to stretch and/or strengthen neck muscles which can be used directly by a patient. There is also a need for a simple method of monitoring the progress of a patient's cervical range of motion that can be performed by the patient.

SUMMARY OF THE INVENTION

The present invention provides an apparatus and method for moving neck muscles. The apparatus comprises a base unit having an upright surface, a top surface and a bottom surface. The upright surface adjoins the bottom surface and the top surface which declines radially to the bottom surface. The base unit can also have an integrated heating source for heating the upright surface and/or the top surface.

The apparatus can have one or more head blockers to limit the range of rotation of a person's head and/or neck. The head blocker is laterally adjustable and is attached to the top surface by an attaching mechanism selected from the group consisting of a sliding mechanism, loop and hook attachment, adjustable bolt and nut mechanism, hinge, pin and slot. The top (or bottom) surface can also have a scale to measure the distance of the head blocker from the midpoint of the base unit to determine the progress of treatment. The top surface can have a channel which is substantially perpendicular to the adjoining line between the upright surface and the top surface. When both the channel and head blockers are present, the head blockers are located on each side of the channel.

The present invention also includes a kit comprising a base unit, as generally described above, and a separate heating unit, such as a heat pack.

The present invention also provides a method for moving neck muscles using the apparatus comprising a base unit having an upright surface, a top surface and a bottom surface, wherein the upright surface adjoins the top surface and the bottom surface, and wherein the top surface declines radially to the bottom surface. The method involves having a person lie on a surface and placing the apparatus underneath the person's neck and head such that the back of the person's head contacts the top surface so that the top surface declines away from the person's head and rotating the person's neck from one side to the other with or without having an external force being applied.

The amount of rotation of the person's head is limited by the placement of adjustable head blockers. As the person's movement of the muscles improves, the head blocker is placed further away from the person's head. And the progress of the person's ability to rotate the neck is measured by the distance of the head blocker from the midpoint of the channel. The distance can be determined by reading a scale that is present on the top (or bottom) surface of the apparatus. Before starting the neck rotation, the person's neck and/or shoulder can be heated to loosen the muscles.

DETAILED DESCRIPTION OF THE INVENTION

Figure 1:
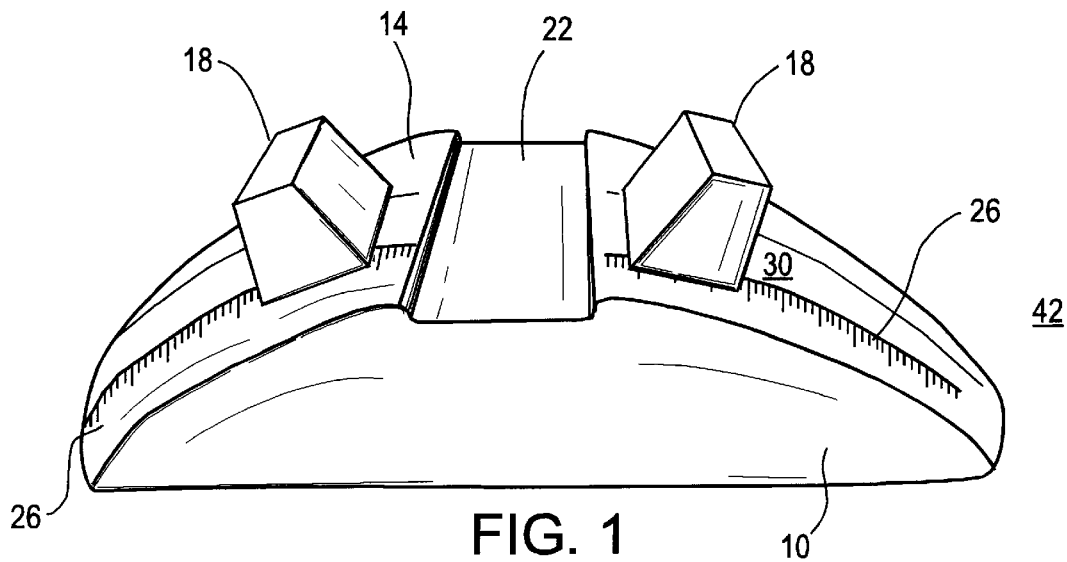
FIG. 1 is a perspective view of an apparatus of the present invention.
Figure 2:
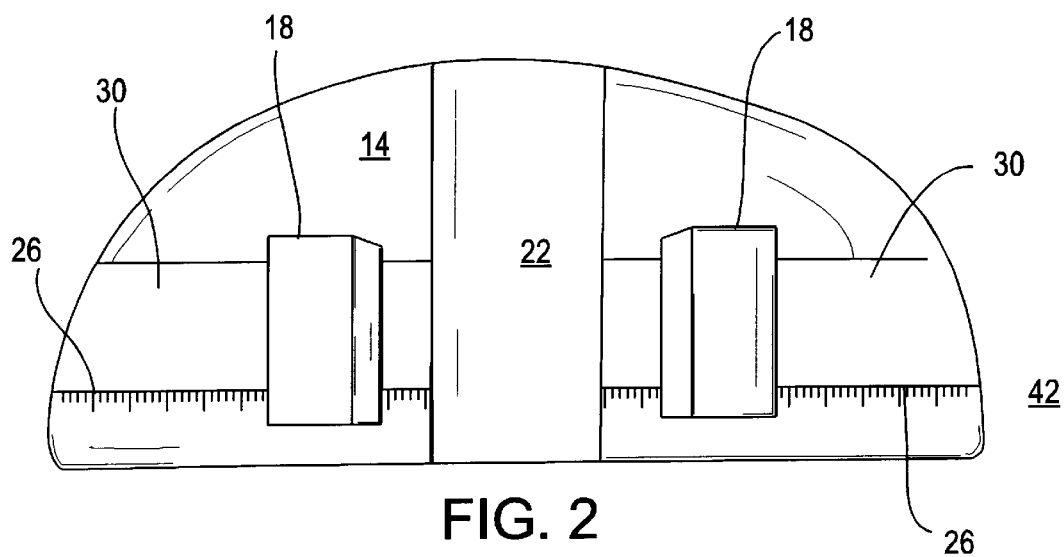
FIG. 2 is a top view of an apparatus of the present invention.
Figure 3:
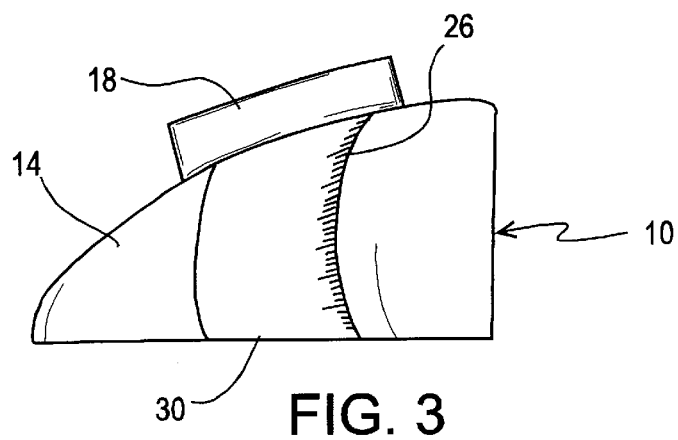
FIG. 3 is a side view of an apparatus of the present invention.
Figure 4:
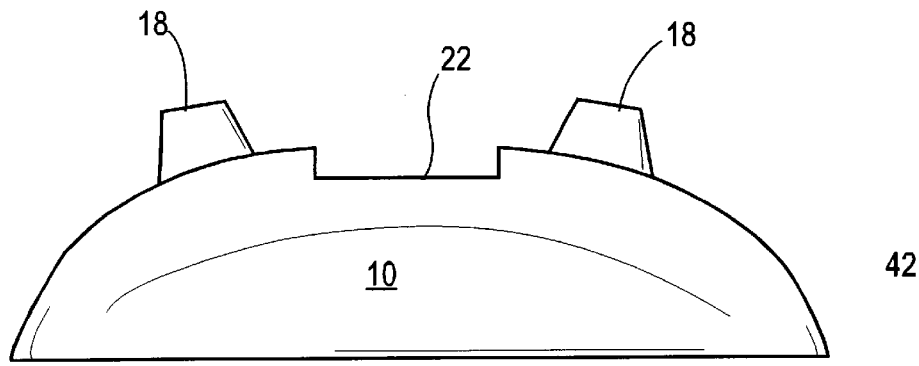
FIG. 4 is an front end view of an apparatus of the present invention.
Figure 5:
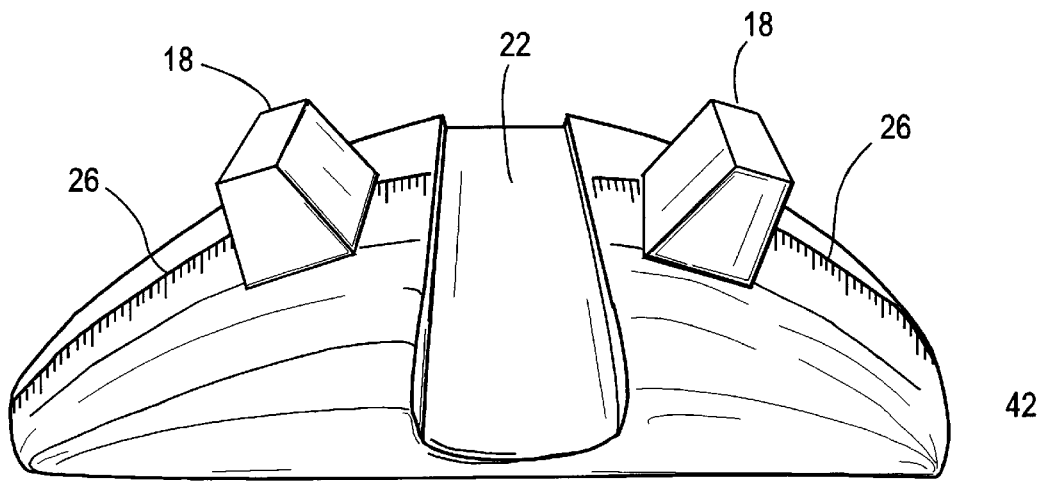
FIG. 5 is a back end view of an apparatus of the present invention.
Figure 6:
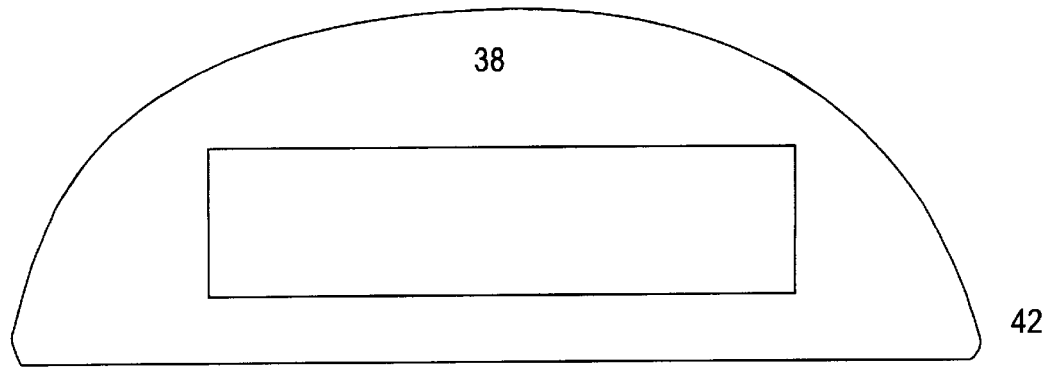
FIG. 6 is a bottom view of an apparatus of the present invention.

The present invention will be described with regard to the accompanying drawings which assist in illustrating various features of the invention. In this regard, the present invention generally relates to a method and an apparatus for moving neck muscles. One embodiment of an apparatus for moving neck muscles is illustrated in FIGS. 1–6. The apparatus comprises a base unit 42 which has an upright surface 10 that adjoins a top surface 14 and a bottom surface 38. Although a wide variety of dimensions are possible, in one embodiment of the present invention the base unit 42 is from about 30 cm to about 40 cm long, from about 10 cm to about 20 cm wide, and from about 5 cm to about 10 cm high.

As used herein, the term "bottom surface" refers to the portion of the base unit 42 which, when the unit is placed on a flat surface, contacts the flat surface. Thus, the bottom surface 38 can be a solid continuous planar surface or if the base unit 42 is hollow, the bottom surface 38 can be defined as the edges or the lip of the upright surface and the top surface which can contact a flat surface. It should be recognized, however, that the apparatus can include feet on the bottom surface 38 of the base unit 42, and thus, the bottom surface 38 may not contact a flat surface on which the apparatus sits.

In use, a patient places his or her head and neck on the top surface of the base unit 42 while moving the neck from one side to the other. The base unit 42 is shaped so that the top surface 14 radially declines to the bottom surface 38 which allows the neck to be rotated substantially coaxially along the neck's own axis. This structure allows the neck muscles to be stretched by rotation without any significant undesired vertical or lateral movement of the neck muscles.

In order to comfortably support the person's head and neck, the upright surface 10 of the base unit 42 is preferably from about 5 cm to about 10 cm high, more preferably from about 6 cm to about 9 cm high, and most preferably from about 7 cm to about 8 cm high.

In one embodiment of the present invention, the height of the base unit 42 is adjustable by having one or more mechanisms for adjusting the height of the apparatus, e.g., feet. The mechanism for adjusting height can be located at the bottom of the upright surface 10, the bottom surface 38, and in cases where the bottom is hollow, on the underside of the top surface 14. Alternatively, the upright surface 10 itself can be made adjustable to provide the desired height adjustment. The height adjustment can be in fixed increments by having a mechanism for discreet incremental adjustment such as a pin and slot like mechanism. Or the height adjustment can be made in infinitely small increments by having a mechanism which can be adjusted in minute increments such as a screw-like mechanism. The bottom of the mechanism for adjusting height can be metal, plastic, rubber, or any other material that can be securely placed on a surface without damaging the surface.

A height adjuster located on or near the upright surface 10 can be an elongated material that has a length that is substantially equal to the length of the upright surface 10 which can be adjusted with one adjusting unit. Or the adjuster can be two or more small support pieces located near the upright surface 10. When two or more adjusters are used near the upright surface 10, the adjusters are spaced apart in a such a manner as to allow steady placement of the base unit on a surface when it is being used by a person.

The top surface 14 declines radially to the bottom surface 38. As used in this invention, the term "radially" refers to both a straight line sloping and a curved sloping of the top surface 14. This gradual radial declining of the top surface 14 allows the person's head to be slightly tilted backward which allows the neck to be rotated substantially coaxially along its own axis. The angle of decline of the top surface 14, measured from the horizontal, in the direction perpendicular to the upright surface 10 is preferably from about 10° to about 20°, more preferably from about 12° to about 15°, and most preferably from about 13° to about 14°. The angle of decline of the top surface 14, measured from the horizontal, along the adjoining portion of top surface 14 and the upright surface 10 is preferably from about 20° to about 30°, more preferably from about 22° to about 28°, and most preferably from about 23° to about 27°.

In another embodiment of the present invention, the angle of decline of the top surface 14, measured from the horizontal, can be adjusted by having one or more mechanisms for independently adjusting the height of the apparatus at different positions on the apparatus. The adjusting mechanism can be located at the bottom of the upright surface 10, the bottom surface 38, and in cases where the bottom is hollow, on the underside of the top surface 14. For example, by having one or more adjusters on or near, i.e., proximal to, the upright surface 10 and another one or more adjusters distal to the upright surface 10, the height of the base unit 42 and the angle of decline of the top surface 14 can be independently adjusted.

The base unit 42 can also have one or more head blockers 18 located on the top surface 14. The head blocker 18 limits the movement of the neck by blocking the rotation of the person's head. The size of head blocker 18 should be large enough to comfortably prevent further rotation of a person's head. Preferably, the head blocker 18 is from at least about 0.5 cm to about 10 cm long (i.e., in length), more preferably from about 1 cm to about 5 cm long, and most preferably from about 1 cm to about 3 long. In addition, the head blocker 18 should be wide enough to provide sufficient resistance to prevent a person from further rotating his or her head after being stopped by the head blocker. Preferably, the head blocker 18 is from at least about 2 to about 10 cm wide, more preferably from at least about 4 to about 8 cm wide, and most preferably from at least about 5 cm to about 6 cm wide.

The possible distance of neck rotation is affected by the height of the head blocker 18. For example, it is obvious that if the head blocker is very low then it would take a greater rotation for a person's head to touch the head blocker compared to a higher head blocker. A finer control of the amount of neck rotation is achieved by having a relatively high head blocker. Thus, it is preferred that the head blocker 18 is from at least about 5 cm to about 15 cm high, more preferably from at least about 8 cm to about 12 high, and most preferably from at least about 10 cm to about 12 high.

In addition, the angle of the head blocker also effects distance of neck rotation as well as the comfort level of using the apparatus. For example, a head blocker that is 90° upright will stop the neck rotation much sooner and will be less comfortable than a head blocker that has angle of 45°. As used in this invention, the angle of a head blocker is defined as the angle of the side of the head blocker to be contacted by a person's head measured from a tangential plane on the top surface 14. To provide a comfortable stopping point with fine neck rotation control, preferably the angle of the head blocker is from about 90° to about 135° more preferably from about 90° to about 120°, and most preferably from about 100° to about 110°.

By having a head blocker 18 which is laterally adjustable, a person can increase or decrease the amount of neck muscle movement depending upon the progress of treatment. Moving the head blocker 18 closer to one's head decreases the amount of neck rotation, and thus, allows smaller neck muscle movement. Moving the head blocker 18 farther away from one's head allows greater neck rotation. The head blocker 18 can be attached to the top surface 14 by any suitable attaching mechanism, such as a sliding mechanism, a loop and hook attachment, an adjustable bolt and nut mechanism, a hinge, a pin or a slot.

The top surface 14 (or the bottom surface 38) can also have a scale 26 for measuring the amount of lateral movement of the head blocker 18. This measuring scale 26 allows a quick and objective method of monitoring the progress of neck movement. The scale 26 can be located anywhere on the top surface 14 as long as the position of head blocker 18 can be easily determined using the scale 26. The scale can be based upon inches, metric system(e.g., centimeter scale), or any other standard or arbitrary measuring units. To allow for fine measurements, the scale 26 should be in increments of no greater than about ½ inch, more preferably no greater than about ¼ inch, and most preferably no greater than about ⅛ inch. If the scale 26 is in metric system than the increments should be no greater than about 2 cm, more preferably no greater than about 1, and most preferably no greater than about 5 mm. Although the progress of improvement in neck motion can be measured from any set point, it is typically determined by measuring the distance of the head blocker 18 from the midpoint of the person's head or the channel 22.

The top surface 14 can have a channel 22 for positioning the person's head and neck, or for inserting a heat pack. As used in this invention, a "channel" is a groove or an indentation present on the top surface of the base unit. The channel 22 is substantially perpendicular to the adjoining line between the upright surface 10 and the top surface 14. In order to comfortably accommodate a person's head and neck, the channel 22 is from about 7 cm to about 12 in width, more preferably from about 8 cm to about 10 cm in width, and most preferably from about 8 cm to about 9 cm in width.

In another embodiment of the present invention, the width of the channel 22 is adjustable by having the base unit 42 made up of two interconnecting units. The two units are divided along the axis perpendicular to the upright surface 10 and are substantially divided in equal portions. One of the interconnecting unit has a slightly larger connecting section which allows it to slide over the other interconnecting unit. The width of the channel 22 is then determined by the amount of overlap between the two interconnecting units. The two interconnecting units can be interconnected by any suitable connecting mechanism, such as a sliding mechanism.

The channel 22 should be sufficiently long enough to allow both the head and neck of a person to be comfortably placed on the channel 22. Preferably the channel 22 is from about 10 cm to about 20 cm in length, more preferably from about 15 cm to about 20 cm in length, and most preferably the channel 22 runs substantially the entire length of the top surface 14 of the base unit 42.

The depth of the channel 22 should be shallow enough to allow a person to rotate the neck without having the movement hindered by the side walls of the channel 22. Alternatively, the channel 22 should be deep enough to allow a heat pack to fit inside the channel 22 and not shift from side to side. Preferably the channel 22 is from about 1 cm to about 3 cm in depth, more preferably from about 1 cm to about 2 cm in depth, and most preferably from about 1.5 cm to about 2 cm in depth.

When both the channel 22 and the head blocker 18 are present on the top surface 14 of the base unit 42, the head blocker 18 is located on the side of the channel 22 and is made adjustable in the direction that is substantially perpendicular to the channel 22.

When using the apparatus of the present invention, the person can be sitting in a couch, in a reclining position, lying on a surface or be in any position where the neck and the head can be comfortably supported by the base unit 42. Surfaces where the apparatus can be used include a floor, a mat, a blanket, a table, a bed, a couch, and any other medium which can securely support the base unit 42 and the person's head and neck.

In one embodiment of the present invention, the base unit 42 has an integrated heating source for heating the upright surface and/or the top surface. This heating source heats the surfaces of the apparatus so that a person's neck and/or shoulder muscles can be loosened prior to moving the muscles. The heating source can be operated by a battery or electricity.

In another embodiment of the present invention, a kit is provided comprising the base unit 42 and a separate heating unit. The heating unit is typically placed in between the person's neck and the upright surface and/or top surface 14 of the base unit to loosen the person's neck and/or shoulder muscles. More preferably, the heating unit is placed into channel 22. Alternatively, the heating unit can be used to heat the person's neck and/or shoulder muscles prior to moving the muscles using the apparatus of the present invention. The heating unit can be any unit that can provide sufficient heat to loosen the person's neck muscles. Heat can be generated chemically, or electrically. Furthermore, the heating unit can be a container having substantially flat dimensions which can be filled with a hot liquid. Or it can simply be a material which can be heated by another source such as a microwave oven, a stove, or a hot air blower such as a hair dryer and placed on the top surface 14.

In the embodiment of a kit, the apparatus can be adapted so that the heating unit, such as a heat pack, can fit into the channel 22 and/or along the upright surface 10. More specifically, the shape and design of the apparatus and heat pack are such that, when engaged, the resulting configuration is appropriate for a patient to comfortably use the device.

The muscles can also be loosened using a medicine such as a muscle relaxant prior to using the apparatus of the present invention. The medicine can be orally or topically active. However, topically active muscle relaxant is preferred to localize the muscle relaxant property to the affected muscles. The medicine can be prescription medicine such as Flexeril®, or Soma or over-the-counter medication such as Bengay®, Flexall®, or Capsaicin.

In order to effectively loosen the muscles without posing a danger of causing a burn, the heat source or the heat unit provides heating temperature in the range of from about 60° C. to about 80° C., more preferably from about 71° C. to about 79° C., and most preferably from about 74° C. to about 75° C. In order to have a beneficial effect, the muscles should be loosened by one or more of the above methods for at least about one minute prior to moving the muscles using the apparatus of the present invention, more preferably at least about 2 minutes, and most preferably at least about 3 minutes.

The base unit 42 can be made of any material which can substantially retain the structural integrity when it is being used by a person. Exemplary materials suitable for the base unit 42 include a molded plastic, rubber, foam, fabric, wood, metal, and combinations thereof. When the base unit 42 comprises a fabric, the fabric is filled with other material which have the shape of the base unit of the present invention. Alternatively, the fabric can be made in the shape of the base unit 42 and be filled with materials. When channel 22 is present on the top surface 14, the channel 22 can be lined with a cushion to provide a comfortable support for the person's head and neck. A cushion can be made of any material that has a sufficiently elastic property as to provide a comfortable support. Exemplary cushion materials include a rubber, foam, fabric, sponge, feathers, cotton, sand, and combinations thereof. When a heating unit is provided with the apparatus of the present invention, the heating unit itself can serve as a cushion.

By applying an external force to the person's head, the apparatus of the present invention can be used to stretch or strengthen neck muscles. For example, by wearing a band around the head, one can attach a small weights, e.g., about one pound weights up to about five pounds, to increase the force of rotation to aid in stretching or strengthening the muscles. In this case, as the head rotates, gravity pulls the head down until the person's head hits the head stopper. This additional force improves stretching. Similarly such an external force can be used to strengthen the muscles. For example, once the person's neck is fully rotated, simply trying to rotate the neck back to the neutral position, i.e., upright position, while wearing the lead weights will help strengthen the neck muscles. Alternatively, by attaching a rubber band or a spring to the head strap and the edge of the base unit 42 a person can perform resistance rotation exercises to strengthen or stretch the muscles. Furthermore, the muscle strengthening can involve an isometric exercise by having a physical therapist or another person place a hand on the head of the person performing the exercise and providing the resistance to the neck rotation.

A further embodiment of the present invention is a method of using the apparatus described herein. More particularly, the method is for moving the neck muscles of a person lying on a surface. This method includes placing the apparatus of the present invention, as generally described herein, underneath the person's neck and head such that the back of the person's head contacts the top surface of the apparatus so that the top surface declines away from the person's head. The method further includes rotating the person's neck from one side to the other. The method can also include other operational procedures, as generally described herein, such as heating neck and shoulder muscles of the person prior to rotating the person's neck and applying an external force to the person's head.

Similarly, by having the apparatus of the present invention which can accommodate a person's arm, leg, ankle, or back the apparatus can be used to treat similar injuries to a person's arm, leg, ankle or back, respectively, as well as allowing stretching and/or strengthening exercises. As well be recognized, the angle of decline on these apparatuses should be adjusted to provide desired and isolated exercise or stretching of a particular muscles without causing undesired motion of the muscles.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method of moving neck muscles of a person lying on a surface comprising the steps of:
   heating neck and shoulder muscles of said person for at least about 1 minute;
   placing an apparatus underneath said person's neck and head, wherein said apparatus consists essentially of a base unit, wherein said base unit comprises an upright surface, a top surface and a bottom surface, wherein said upright surface adjoins said top surface and said bottom surface and wherein said top surface declines away from said upright surface in directions perpendicular to said upright surface and declines along the adjoining portion of said top surface and said upright surface in directions along said upright surface; such that the back of said person's head contacts said top surface so that said top surface declines away from said person's head; and
   rotating said person's neck from one side to the other after said step of heating neck and shoulder muscles of said person.

2. The method of claim 1, wherein said apparatus further comprises a laterally adjustable head blocker and wherein said step of moving neck muscles comprises rotating said person's neck from one side to the other to the extent of said head blocker.

3. The method of claim 2, further comprising the step of moving said head blocker away from said person's head.

4. The method of claim 2, wherein the progress of said rotation of said person's neck is measured by the distance of said head blocker from a midpoint of said channel.

5. The method of claim 1, wherein said person's neck is rotated substantially coaxially along its own axis.

6. The method of claim 1, further comprising the step of applying an external force to said person's head.

7. The method of claim 1, wherein said method of moving said person's neck muscles is used to strengthen said person's neck muscles by applying an external force to said person's head.

8. The method of claim 1, wherein said method of moving said person's neck muscles is used as a neck muscle stretching exercise by applying an external force to said person's head.

9. An apparatus for moving neck muscles consisting essentially of:
   a base unit, wherein said base unit comprises an upright surface, a top surface and a bottom surface, wherein said upright surface adjoins said top surface and said bottom surface and wherein said top surface declines radially away from said upright surface in directions perpendicular to said upright surface and declines radially along the adjoining portion of said top surface and said upright surface in directions along said upright surface;

a laterally adjustable head blocker; and wherein said top surface of said base unit has a scale for measuring lateral movement of said head blocker.

10. The apparatus of claim 1, wherein said top surface comprises a channel substantially perpendicular to the adjoining line between said upright surface and said top surface.

11. The apparatus of claim 10, wherein said apparatus comprises a head stopper located on each side of said channel.

12. The apparatus of claim 1, wherein said apparatus comprises a heat source for heating said upright surface or said top surface.

13. The apparatus of claim 1, wherein said apparatus comprises molded plastic.

14. The apparatus of claim 1, wherein said apparatus comprises a foam material.

15. The apparatus of claim 1, wherein said apparatus comprises a fabric.

16. A kit comprising the apparatus of claim 1 and a heating unit.

17. An apparatus for moving neck muscles consisting essentially of a base unit, wherein said base unit comprises:

an upright surface, a top surface and a bottom surface, wherein said upright surface adjoins said top surface and said bottom surface and wherein said top surface declines radially away from said upright surface in directions perpendicular to said upright surface and declines radially along the adjoining portion of said top surface and said upright surface in directions along said upright surface, and wherein said top surface comprises a channel substantially perpendicular to the adjoining line between said upright surface and said top surface;

a laterally adjustable bead blocker located on each side of said channel of said top surface, wherein said top surface has a scale for measuring lateral movement of said head blocker; and a heat source for heating said upright surface, said top surface, or both said upright surface and said top surface.

18. The apparatus of claim 17, wherein said apparatus comprises molded plastic.

19. The apparatus of claim 17, wherein said apparatus comprises a foam material.

20. The apparatus of claim 17, wherein said apparatus comprises a fabric.

* * * * *